(12) United States Patent
Bieneman (10) Patent No.: US 7,655,013 B2
(45) Date of Patent: Feb. 2, 2010

(54) SNARE RETRIEVAL DEVICE (76) Inventor: Bruce Kirke Bieneman, 9043 Clayton Rd., Saint Louis, MO (US) 63117

( * ) Notice: Subject to any disclaimer, the term of this patent is extended or adjusted under 35 U.S.C. 154(b) by 442 days.

(21) Appl. No.: 11/428,996

(22) Filed: Jul. 6, 2006

(65) Prior Publication Data

US 2008/0009883 A1    Jan. 10, 2008

(51) Int. Cl.
    *A61F 11/00* (2006.01)
(52) U.S. Cl. .................. 606/108; 606/113; 606/127
(58) Field of Classification Search .................. 606/106, 606/108–113
    See application file for complete search history.

(56) References Cited

U.S. PATENT DOCUMENTS

| | | | |
|---|---|---|---|
| 3,435,826 A | 4/1969 | Fogarty | |
| 3,521,620 A | 7/1970 | Cook | |
| 4,538,622 A | 9/1985 | Samson et al. | |
| 5,171,233 A | 12/1992 | Amplatz et al. | |
| 5,376,094 A | 12/1994 | Kline | |
| 5,387,219 A | 2/1995 | Rappe | |
| 5,947,995 A | 9/1999 | Samuels | |
| 5,972,019 A | 10/1999 | Engelson et al. | |
| 6,299,612 B1 * | 10/2001 | Ouchi | 606/47 |
| 6,402,771 B1 | 6/2002 | Palmer et al. | |
| 6,458,145 B1 | 10/2002 | Ravenscroft et al. | |
| 6,517,551 B1 | 2/2003 | Driskill | |
| 6,554,842 B2 | 4/2003 | Heuser et al. | |
| 6,592,607 B1 | 7/2003 | Palmer et al. | |
| 6,641,590 B1 | 11/2003 | Palmer et al. | |
| 6,652,536 B2 * | 11/2003 | Mathews et al. | 606/113 |
| 6,660,021 B1 | 12/2003 | Palmer et al. | |
| 6,679,893 B1 | 1/2004 | Tran | |
| 6,695,865 B2 | 2/2004 | Boyle et al. | |
| 6,793,664 B2 | 9/2004 | Mazzocchi et al. | |
| 6,878,151 B2 | 4/2005 | Carrison et al. | |
| 2001/0031981 A1 | 10/2001 | Evans et al. | |
| 2002/0188262 A1 | 12/2002 | Abe | |
| 2004/0116960 A1 | 6/2004 | Demond et al. | |
| 2004/0153119 A1 | 8/2004 | Kusleika et al. | |
| 2004/0225299 A1 | 11/2004 | Carrison et al. | |

OTHER PUBLICATIONS

Medical Device Technologies Inc., Product Information Sheet for Mini EnSnare System, Gainesville, Florida.
Medical Device Technologies Inc., Product Information Sheet for En Snare System, Gainesville, Florida.
Boston Scientific Target; Product Information Sheet for Retriever—10 Endovascular Snare; Cork, Ireland.
Boston Scientific Target, Product Information Sheet for In Time Retriever Device, Fremont, California.
EV3 an Endovascular Company, Product Information Sheet for Amplatz Goose Neck MicroSnare Kit, Plymouth, Minnesota.

* cited by examiner

*Primary Examiner*—Todd E Manahan
*Assistant Examiner*—Kevin Everage
(74) *Attorney, Agent, or Firm*—McGarry Bair PC (57) ABSTRACT A snare for retrieving objects from a body cavity during a medical procedure comprises a guide element having a proximal end and a distal end, a loop provided on the guide element near the distal end and a flexible element provided on the guide element near the distal end and forming a tip.

26 Claims, 5 Drawing Sheets

SNARE RETRIEVAL DEVICE

BACKGROUND OF THE INVENTION

1. Field of the Invention

The invention relates generally to a medical device, and more particularly to a retrieval device for capturing and/or removing objects from within a body cavity.

2. Description of the Related Art

Medical retrieval devices used to remove objects from body cavities by inserting the retrieval device, usually by way of a catheter, into a body cavity, engaging the object using the retrieval device, and removing the object using the retrieval device, or at least moving the object to more accessible location within the body. The object to be retrieved can be a natural formation in the body, such as a blood clot, kidney stone, gall stone, or polyp or a foreign item such as a coil, stent, catheter, or guidewire. The three most common retrieval devices are basket retrieval devices, forceps retrieval devices, and snare loop retrieval devices.

A common application of medical retrieval devices is removing objects from the neurovasculature during a medical procedure, for example, removing clots during the setting of acute stroke or removing displaced coils used in the management of intracranial aneurysm. Yet, the neurovasculature poses a problem for known medical retrieval devices since the neurovasculature is smaller and more tortuous than other body cavities. Forceps retrieval devices are used primarily in larger cavities and are typically too large and rigid to be used in the neurovasculature. Other basket and snare loop retrieval devices are too stiff for neurovasculature application. The stiffness or rigidity of known medical retrieval devices is especially problematic at the leading distal end of the medical retrieval device. As the retrieval device is threaded through the vessel, the leading distal end can damage the delicate walls of the vasculature. However, a certain amount of stiffness for the proximal end of the retrieval device is necessary so that the user (i.e. physician) can manipulate and guide the retrieval device through the body cavity.

SUMMARY OF THE INVENTION

A snare for retrieving objects during a medical procedure is provided, wherein the snare comprises a guide element having a proximal end and a distal end, a loop provided on the guide element near the distal end and a flexible element provided on the guide element near the distal end and forming a tip.

The flexible element can extend distally of the loop. The flexible element can be one of a single strand, braid, and coil/core configuration. The flexible element can comprise a blunt distal end.

The guide element and at least one of the loop and the flexible element can be formed from a common wire. The other of the loop and the flexible element can be mounted to the common wire. The common wire can be one of a single strand, braid, and coil/core configuration. The common wire can be a braid. The flexible element can extend distally of the loop. The flexible element can have a coil/core configuration. The flexible element can comprise a blunt distal end.

At least a portion of the snare is radiopaque. The portion of the snare can be made of a noble metal.

The snare can be sized to be received in the neurovasculature. The loop can have a fixed diameter. The diameter of the loop can be between 2.5 and 4 mm. The loop can have an adjustable diameter.

At least one of the guide element, loop, and flexible element can be made from a shape memory material.

According to another aspect of the invention, a medical retrieval apparatus for retrieving objects during a medical procedure comprises a snare having a guide element having a proximal and a distal end, a loop provided on the guide element near the distal end and a flexible element provided on the guide element near the distal end and forming a tip, and a catheter defining a lumen for receiving the snare.

The flexible element can extend distally of the loop. The flexible element is one of a single strand, braid, and coil/core configuration. The flexible element can comprise a blunt distal end.

The guide element and at least one of the loop and the flexible element can be formed from a common wire. The other of the loop and the flexible element can be mounted to the common wire. The common wire can be one of a single strand, braid, and coil/core configuration.

At least a portion of the snare can be radiopaque. The snare can be sized to be received in the neurovasculature. At least one of the guide element, loop, and flexible element can be made from a shape memory material.

DESCRIPTION OF THE PREFERRED EMBODIMENT

Figure 1:
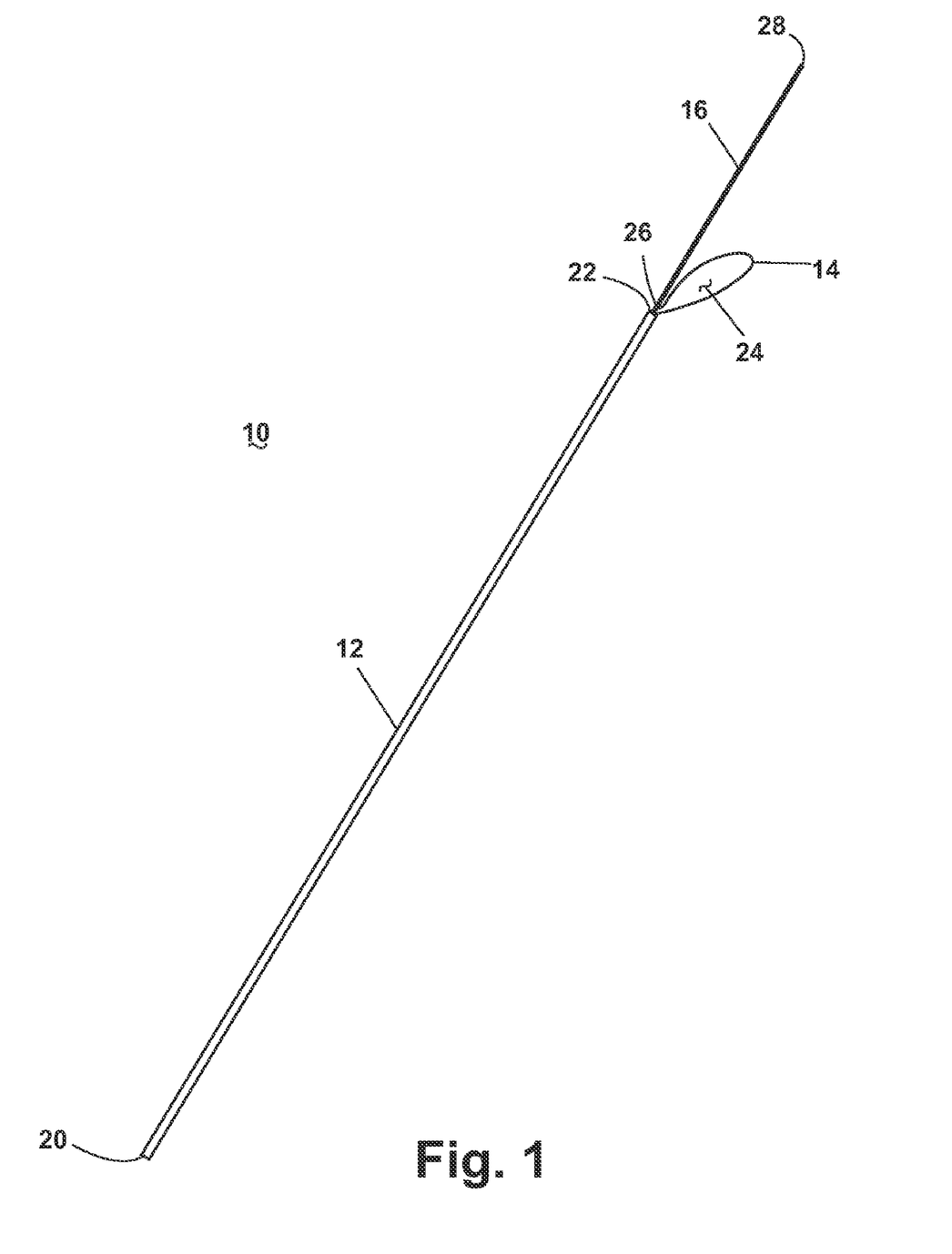
FIG. 1 is a schematic illustration of a general first embodiment of a snare according to the present invention.

Referring to the drawings, and in particular to FIG. 1, a general or schematic first embodiment of a snare 10 according to the invention is shown is illustrated. The snare 10 comprises a guide element 12, a loop 14, and a flexible element 16. The snare 10 is used to retrieve objects from body cavities, including organs, vessels, passages and orifices, during a medical procedure by capturing or otherwise engaging the object to be retrieved using the loop 14. The snare is manipulated by a user performing the medical procedure using the guide element 12 to position the loop 14 relative to the object to be retrieved. The snare 10 can be used to retrieve objects from the body including, but not limited to, foreign objects such as coils, balloons, beads, guidewires, catheters, and other embolic devices, and objects that naturally form within the body, such as blood clots, kidney stones, gall stones, and polyps. It is understood that the drawings are not drawn to scale and that certain features of the snare 10 are enlarged with respect to other features to illustrate the details of the invention.

The guide element 12 comprises an elongated wire having a proximal end 20 and a distal end 22. The loop 14 and flexible element 16 are provided on the wire near the distal end 22. The wire can have one of a number of various configurations that are commonly known in the medical device art. The wire can have a single strand configuration, which can include a single strand of wire that is folded back upon itself, a braided or cable configuration, where multiple strands are braid, twisted, or otherwise treaded together, or a coil/core configuration, where a coil of wire is wrapped around a core wire of material.

The proximal end 20 of the guide element 12 typically remains outside the body or body cavity during a medical procedure and is used to maneuver the snare 10 through the body cavity. The guide element 12 can have a torque device (not shown) located on the proximal end 20 to enable easier manipulation of the snare 12. Such torque devices can be in the form for a grip or handle held by the user, such as is disclosed in U.S. Pat. No. 5,376,094 to Kline, issued Dec. 27, 1994, which is incorporated herein by references in its entirety. The guide element 12 is sufficiently flexible to follow the path of the body cavity into which it is inserted. The guide element 12 can be made of any biocompatible material, such as, but not limited to, stainless steel, tungsten, platinum, gold, titanium, nickel, or any alloys thereof.

The loop 14 comprises a wire that is curved or doubled over to create an opening 24 that is used to ensnare an object to be retrieved. The wire can comprise a single strand configuration, a braided or cable configuration, or a coil/core configuration. The loop 14 is preferably circular or elliptical in shape but can have other geometric configurations. The loop 14 can be provided at any angle with respect to the guide element 12.

The loop 14 can have a fixed opening size or an adjustable opening size. For a fixed opening size, the snare 10 can be made by folding a wire back upon itself, forming a loop shape at the folded end, and securing the free ends of the wire together such that one end cannot substantially move relative to the other end. The free ends can be secured using an adhesive or can be bonded using a welding or brazing process. A sheath can be used to secure ends together without physically attaching the ends together, for example by using a sheath made of shrinkwrap material that tightly encases the ends of the wire. Alternately, the free ends of the wire can be twisted together. The secured ends can form, at least in part, the guide element 12, such that the loop 14 and guide element 12 are continuously formed with one another. Alternately, the loop 14 can be separately attached to the guide element 12. Attachment to the guide element 12 can be accomplished by soldering, brazing, a crimped sleeve, or by using an adhesive such as an epoxy resin.

For an adjustable opening size, the ends of the wire making up the loop 14, whether they form the guide element 12 or not, can move relative to one another to change the opening size of the loop 14. Movement can be accomplished through a mechanically actuated device, such as one incorporated into a handle on the proximal end 20 of the guide element 12.

At least the loop 14 of the snare 10 is preferably made of a shape memory alloy, although it is within the scope of the invention for the guide element 12 and/or the flexible element 16 to also be made of a shape memory alloy. As is well known in the art of articles using shape memory alloys, the loop 14 is subjected to a heat treatment process that defines the "remembered" loop shape. Subsequently, the loop 14 can be elastically deformed, but is very difficult to permanently plastically deform the loop 14. The shape memory effect can be thermally triggered, such as by lowering the temperature of the loop 14 before inserting the snare 10 into the body or by applying heat to the snare 10 once it is in the body, or the shape memory effect can be stress-induced, such as by forcing the snare 10 through a catheter have a diameter smaller than the "remembered" loop diameter. As the loop 14 is forced through the catheter, the loop 14 will be compressed by the confines of the catheter wall. When the loop 14 emerges from the catheter, it will automatically uncompress and regain its "remembered" shape. A preferred shape memory alloy is a nickel-titanium alloy or Nitinol. Other examples of suitable shape memory alloys include copper-zinc-aluminum, copper-aluminum-nickel, titanium-palladium-nickel, nickel-titanium-copper, gold-cadmium, iron-manganese-silicon, iron-zinc-copper-aluminum, titanium-niobium-aluminum, uranium-niobium, hafnium-titanium-nickel, nickel-iron-zinc-aluminum, copper-aluminum-iron, titanium-niobium, zirconium-copper-zinc, and nickel-zirconium-titanium.

The flexible element 16 is attached to the loop 14 or guide element 12 at a proximal end 26 and preferably extends distally of the loop 14 to form a distal leading end 28 on the snare 10. The flexible element 16 can be formed continuously or integrally with the guide element 12 by a common wire, or the flexible element 16 can be separately attached, for example, by bonding the flexible element 16 to the guide element 12 near the distal end of the wire. The flexible element 16 can comprise a wire having a single strand configuration, a braided or cable configuration, or a coil/core configuration. The flexible element 16 is configured to serve as an atraumatic leading tip as the snare 10 is inserted through a body cavity. One such atraumatic configuration comprises a blunt or rounded tip on the most distal end 28 of the flexible element 16.

The snare 10 is preferably readily imaged using contemporary imaging techniques. For example, at least a portion of the snare 10 can be made of material suitable to be imaged using X-ray, mammography, ultrasound, fluoroscopy, computed tomography, magnetic resonance imaging (MRI), computerized axial tomography (CAT) scan, Doppler, radiation detector, and any possible combination thereof. Preferably, a portion of the snare 10 is radiopaque. To enhance radiopacity, a portion of the snare 10 can be made of or coated with a noble metal such as gold or platinum. In one preferred embodiment, the loop 14 is coated with gold for increased radiopacity and the flexible element 16 is made of platinum.

The snare 10 can be utilized in various retrieval procedures, and is particularly suited to neurovascular applications. Exemplary dimensions of the snare 10 suitable for neurovascular applications are a guide element 12 having a length of 150 cm and a diameter of 0.356 to 0.381 mm, a loop 14 having an opening size of 2.5 to 4.0 mm, and a flexible element 16 having a length of 3 to 4 mm and a diameter of 0.330 mm. For other applications, the elements of the snare 10 can have other dimensions. An exemplary catheter for use with the snare 10 is a 3 French catheter with an outer diameter of 0.027 inches, an inner diameter of 0.021 to 0.025 inches, and a length of 140 cm.

Figure 2:
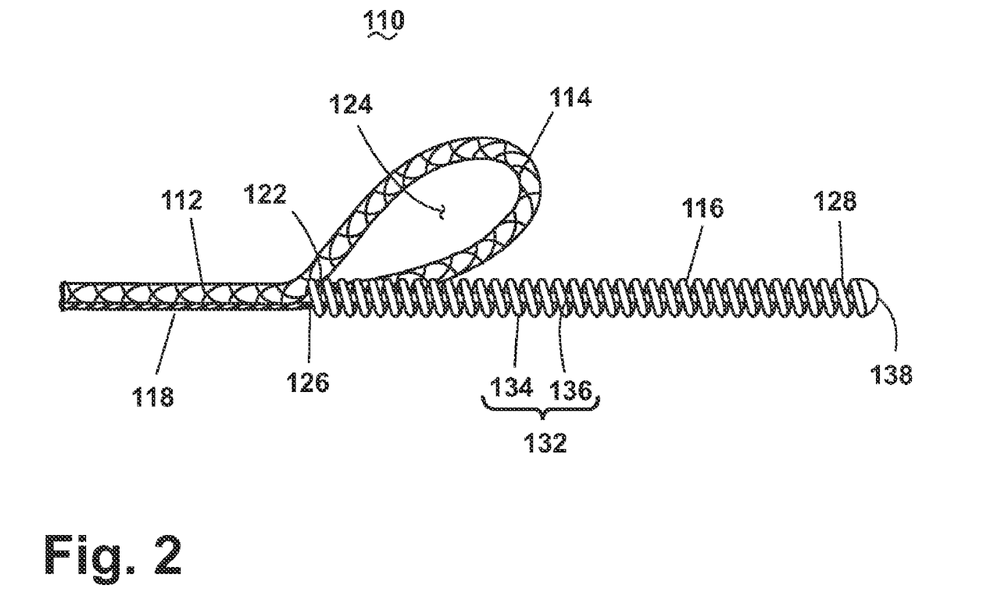
FIG. 2 is a schematic illustration of a second embodiment of the snare according to the invention.

Referring to FIG. 2, a second embodiment of the snare 110 according to the invention is illustrated, where like elements are identified by like numerals increased by 100. The snare 110 comprises a guide element 112, a loop 114, and a flexible element 116. The guide element 112 comprises a proximal end 120 (FIG. 3) and a distal end 122. The loop 114 is provided near the distal end 122 of the guide element 112 and comprises an opening 124 having a fixed size. The guide element 112 comprises a braided wire 118, preferably made of Nitinol. The loop 114 comprises a braided Nitinol wire 130 as well and can be continuously formed with the guide element 112 from a common wire. At least the loop 114 of the snare 110 is coated with gold to enhance the imageability of the snare 100. The flexible element 116 comprises a wire 132 having a proximal end 126 and a distal end 128. The proximal end 126 of the flexible element 116 is bonded to the guide wire 112 near or on the distal end 122. The distal end 128 of the flexible element 116 projects beyond the loop 114 to form a leading tip for the snare 110. The wire 132 comprises a coil/core configuration and is made up of a coil 134 wrapped around a generally straight core 136 and further has a blunt, rounded tip 138 located on the distal end 128 of the flexible element 116 that serves as an atraumatic leading tip for the snare 10. The flexible element 116 is preferably constructed from platinum.

Figure 3:
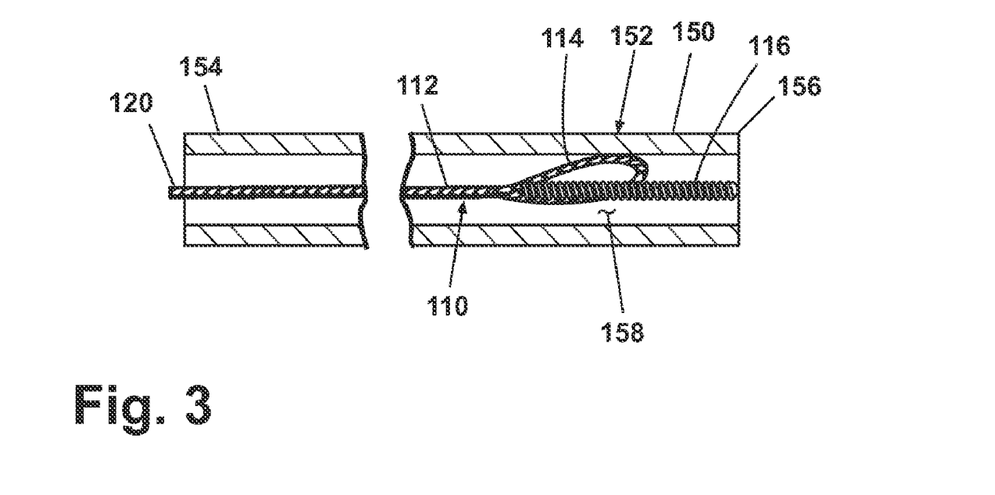
FIG. 3 is a schematic sectional view of the snare from FIG. 2 illustrated as part of a retrieval system that includes a catheter.
Figure 4:
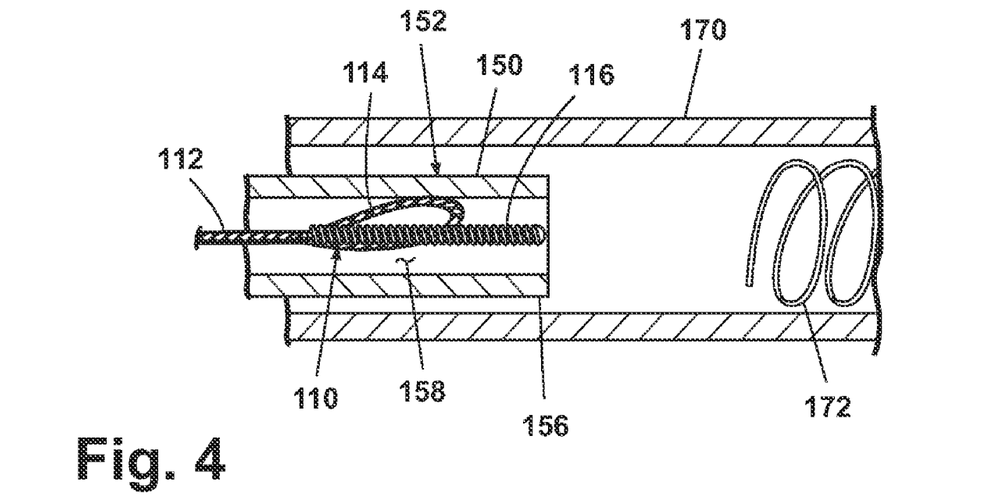
FIG. 4 is a schematic sectional view of the retrieval system from FIG. 3 illustrated within a body cavity.

Referring to FIG. 3, the snare 110 is used in conjunction with a catheter 150 to collectively form a medical retrieval apparatus 152. The catheter 150 has an open proximal end 154 and an open distal end 156 and defining a lumen 158 in which the snare 110 is received. The loop 14 of the snare will be in a collapsed configuration as it is inserted through the catheter 150. The catheter 150 is sized and structured according to its application. For example, for neurovascular applications, the catheter 150 is sized and structured to be inserted into the neurovasculature which comprises small and tortuous vessels and will be sufficiently small and flexible to be inserted through the neurovasculature. The catheter 150 preferably comprises optimally thin walls to minimize the overall size of the medical retrieval apparatus 152. The catheter 150 preferably is made of a polymeric resin impregnated with a braided Nitinol frame.

Figure 5:
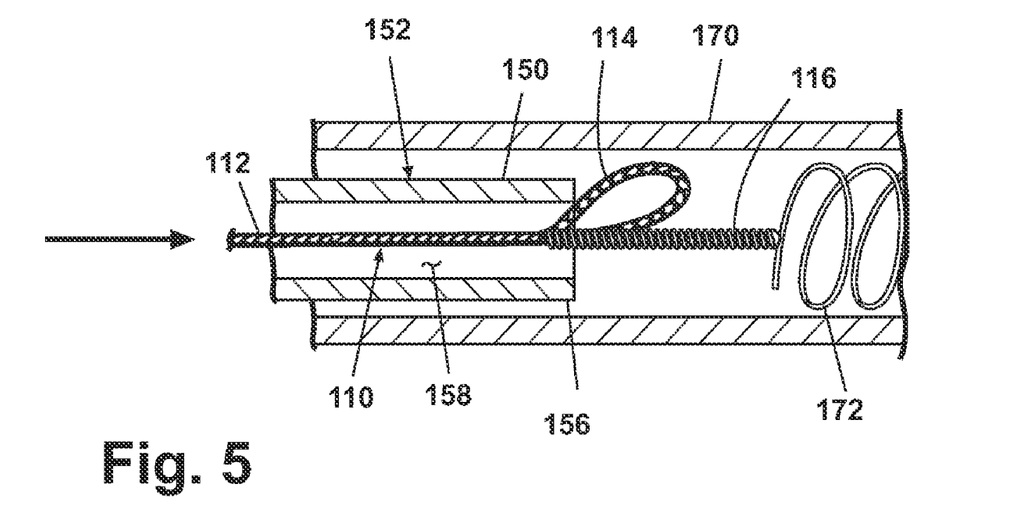
FIG. 5 is a view similar to FIG. 4, where the snare is illustrated distally extended from the catheter.
Figure 6:
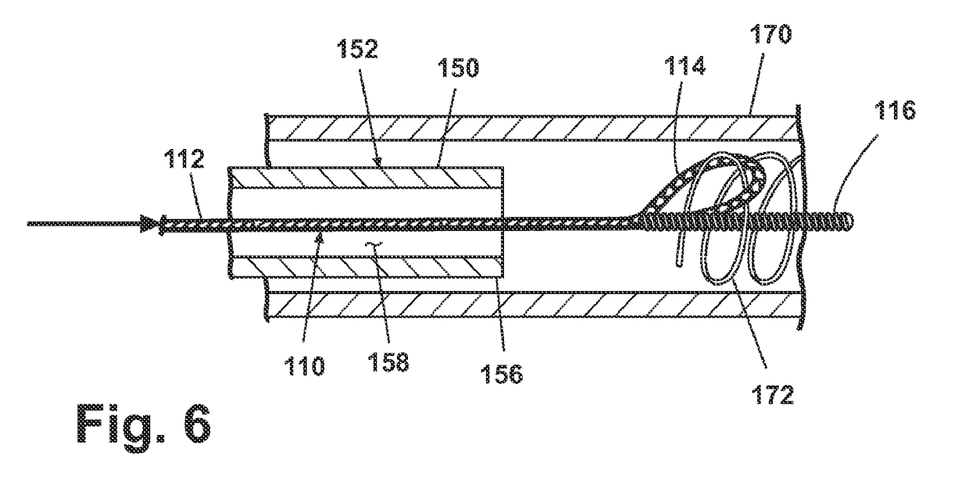
FIG. 6 is a view similar to FIG. 4, where the snare is illustrated as having captured an object to be retrieved from the body cavity.
Figure 7:
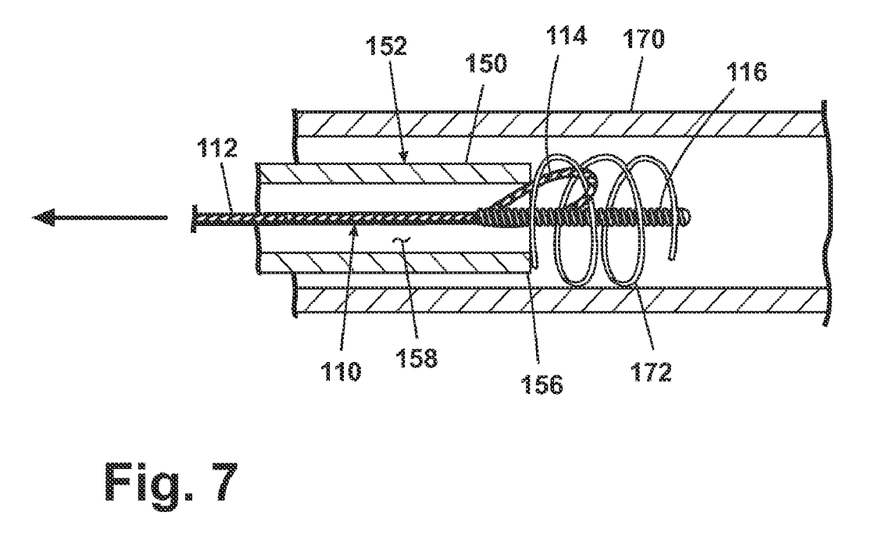
FIG. 7 is a view similar to FIG. 4, where the snare and captured object are illustrated as retracted against the catheter for subsequent removal.

An exemplary method of using the system is illustrated in FIGS. 4-7, using the snare from FIG. 2. The catheter 150 inserted into a body at an entry site, such as surgical incision or a body orifice and threaded through a body cavity 170, such as a blood vessel. The catheter 150 is properly positioned relative to the object 172 to be retrieved, such as a coil. The snare 110 may be preloaded in the lumen 158 prior to insertion of the catheter 150 or the snare 110 may be subsequently inserted into the lumen 158 via the proximal end 154 of catheter 150 after the catheter 150 is in position. In either case, as the snare 110 is inserted into the lumen 158, the loop 114 will be compressed. The proximal end 120 (FIG. 3) of the snare 110 is manipulated by the user by generally advancing the guide element 112 distally with respect to the catheter 150 such that the snare 110 emerges from the open distal end 156 of the catheter 150, as illustrated in FIG. 5. The flexible element 116 emerges first to provide an atraumatic leading feature of snare 110. The loop 114 emerges next and expands to its "remembered" shape. The loop 114 is then positioned relative to the object 172 to be retrieved, as illustrated in FIG. 6, and the snare 110 is maneuvered such that the loop 114 ensnares at least a portion of the object 172. Once the loop 114 ensnares the object 172, the object 172 is captured by either retracting the proximal end 120 of snare 110 or by advancing the catheter 150 over the snare 110. If the object 172 is small enough, the object 172 and snare 110 may be pulled completely into the lumen 158 of the catheter 150. If the object 172 is larger than the opening in the distal end 156, the snare 110 will be retracted such that the object 172 is braced against the catheter 150, as illustrated in FIG. 7. The entire retrieval system 152, including the captured object 172, is then at least partially retracted from the body cavity 170. If the object 172 is small enough, the retrieval system 152 and object 172 can be retracted through the entry site. If object 172 is larger, the retrieval system 152 is retracted to a location within the body where the object 172 is accessible to be surgically removed.

Figure 8:
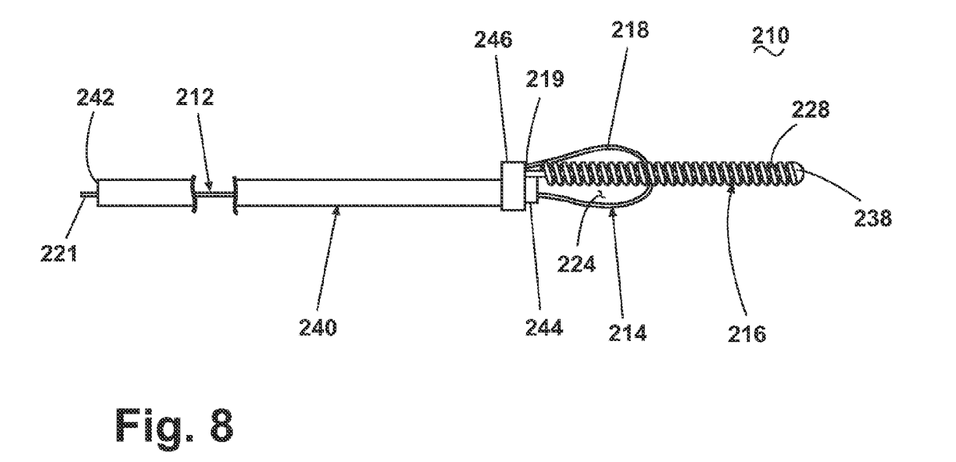
FIG. 8 is a schematic illustration of a third embodiment of the snare according to the invention.

Referring to FIG. 8, a third embodiment of the snare 210 according to the invention is illustrated, where like elements are identified by like numerals increased by 200. The snare 210 comprises a guide element 212, a loop 214, a flexible element 216, and a hollow cannula 240. The cannula 240 comprises an open proximal end 242 and an open distal end 244. The loop 214 is formed continuously with the guide element 212 from a common wire 218, preferably a braided Nitinol wire, by fixing a first end 219 of the wire to the open distal end 244 of the cannula 240 and threading a second end 221 of the wire 218 back through the hollow cannula 240 such that it extends beyond the open proximal end 242 of the cannula 240 for manipulation by the user. The opening 224 in the loop 214 is adjustable in size through manipulation of the second end 221. By moving the second end 221 in a distal direction relative to the cannula 240, the opening 224 will increase in size or diameter. By moving the second end 221 in a proximal direction relative to the cannula 240, the opening 224 will decrease in size or diameter. The wire 218 can be secured to the cannula 240 using a band 246 that extends around the circumference of the cannula 240. The proximal end 226 of the flexible element 216 is secured to the distal end 244 of the cannula 240 and can be adjacent to the wire 218. The flexible element 216 can be secured to the cannula 240 by the band 246.

Figure 9:
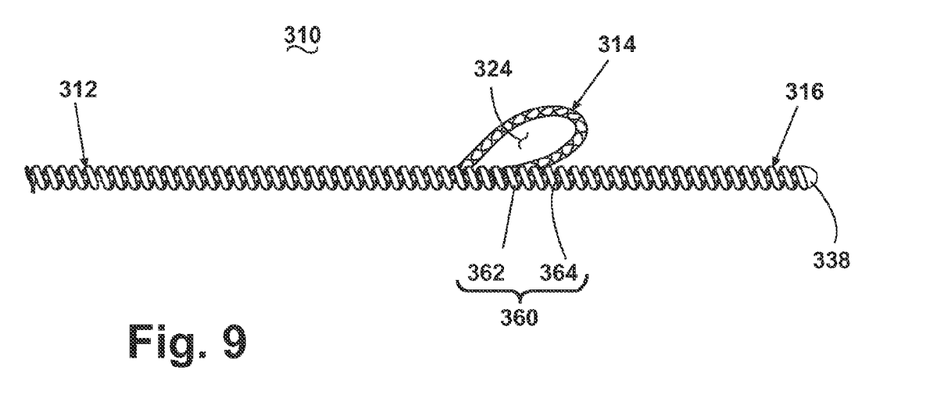
FIG. 9 is a schematic illustration of a fourth embodiment of the snare according to the invention.

Referring to FIG. 9, a fourth embodiment of the snare 310 according to the invention is illustrated, where like elements are identified by like numerals increased by 300. The snare 310 comprises a guide element 312, a loop 314, and a flexible element 316. The flexible element 316 is formed continuously with the guide element 312 from a common wire 360. The wire 360 comprises a coil/core configuration and is made up of a coil 362 wrapped around a generally straight core 364 and further has a blunt, rounded tip 338 located on the distal end 328 of the flexible element 316 that serves as an atraumatic leading tip for the snare 310. The loop 314 is provided on the guide element 312 and comprises an opening 324 having a fixed size. The loop 314 comprises a braided Nitinol wire 330 that is bonded to the guide element 312 such that the portion of the wire 360 making up the flexible element 316 extends distally of the loop 314. While the guide element 312 and flexible element 316 are illustrated as having the same diameter, it is understood that the flexible element 316 can have a smaller diameter than the guide element 312 or vice versa.

The snare 10, 110, 210, 310 is finely dimensioned and flexible due to a combination of the utilization of a simple loop 14, 114, 214, 314 to capture the object to be retrieved and the materials used to make the snare 10, 110, 210, 310. The addition of the flexible element 16, 116, 216, 316 provides the snare 10, 110, 210, 310 with a distal leading tip that is configured to be less traumatic than such a snare alone. The atraumatic configuration of the flexible element 16, 116, 216, 316, which can include the blunt tip as well as the aforementioned flexibility, offers particular advantages in applications where the object to be retrieved is located in a small and/or tortuous body cavity, such as when performing neurointerventional procedures, although it can be used in any application where a flexible leading tip is desirous. More specifically, the combination of an atraumatic, flexible snare and a flexible catheter will provide improved clot retrieval in the setting of acute stroke and removal of displaced coils used in the management of intracranial aneurysms as compared with existing retrieval devices. The loop 14, 114, 214, 314 and flexible element 16, 116, 216, 316 can be imageable to provide accurate localization of the snare 10, 110, 210, 310 within a body cavity. The snare 10, 110, 210, 310 can be readily used with existing retrieval apparatus. While only the snare 110 is shown as part of a retrieval apparatus, it is understood that any embodiment of the snare of the invention can work in a similar manner.

While the invention has been specifically described in connection with certain specific embodiments thereof, it is to be understood that this is by way of illustration and not of limitation, and the scope of the appended claims should be construed as broadly as the prior art will permit.

What is claimed is:

1. A snare for retrieving objects during a medical procedure, consisting essentially of:
    a guide element having a proximal end and a distal end;
    a loop provided on the guide element near the distal end; and
    a flexible element connected directly to the guide element near the distal end and forming a tip.

2. The snare according to claim 1, wherein flexible element extends distally of the loop.

3. The snare according to claim 2, wherein the flexible element comprises a blunt distal end.

4. The snare according to claim 3 wherein the flexible element is one of a single strand, braid, and coil/core configuration.

5. The snare according to claim 1, wherein the guide element and at least one of the loop and the flexible element are formed from a common wire.

6. The snare according to claim 5, wherein the other of the loop and the flexible element is mounted to the common wire.

7. The snare according to claim 6 wherein the common wire is one of a single strand, braid, and coil/core configuration.

8. The snare according to claim 7 wherein the flexible element extends distally of the loop.

9. The snare according to claim 8 wherein the flexible element has a coil/core configuration.

10. The snare according to claim 9, wherein the flexible element comprises a blunt distal end.

11. The snare according to claim 1 wherein at least a portion of the snare is radiopaque.

12. The snare according to claim 1, wherein the snare is sized to be received in the neurovasculature.

13. The snare according to claim 12 wherein the loop has a fixed opening size.

14. The snare according to claim 13 wherein the opening size of the loop is between 2.5 and 4 mm.

15. The snare according to claim 12 wherein the loop has an adjustable perimeter.

16. The snare according to claim 1 wherein at least one of the guide element, loop, and flexible element is made from a shape memory material.

17. A medical retrieval apparatus for retrieving objects during a medical procedure, comprising:
    a snare, consisting essentially of:
        a guide element having a proximal and a distal end;
        a loop provided on the guide element near the distal end; and
        a flexible element connected directly to the guide element near the distal end and forming a tip; and
    a catheter defining a lumen for receiving the snare.

18. The medical retrieval apparatus according to claim 17, wherein the flexible element extends distally of the loop.

19. The medical retrieval apparatus according to claim 18, wherein the flexible element comprises a blunt distal end.

20. The medical retrieval apparatus according to claim 19 wherein the flexible element is one of a single strand, braid, and coil/core configuration.

21. The medical retrieval apparatus according to claim 17, wherein the guide element and at least one of the loop and the flexible element are formed from a common wire.

22. The medical retrieval apparatus according to claim 21, wherein the other of the loop and the flexible element is mounted to the common wire.

23. The medical retrieval apparatus according to claim 21 wherein the common wire is one of a single strand, braid, and coil/core configuration.

24. The medical retrieval apparatus according to claim 17 wherein at least a portion of the snare is radiopaque.

25. The medical retrieval apparatus according to claim 17, wherein the snare is sized to be received in the neurovasculature.

26. The medical retrieval apparatus according to claim 17 wherein at least one of the guide element, loop, and flexible element is made from a shape memory material.

* * * * *

UNITED STATES PATENT AND TRADEMARK OFFICE
CERTIFICATE OF CORRECTION

| | | |
|---|---|---|
| PATENT NO. | : 7,655,013 B2 | Page 1 of 1 |
| APPLICATION NO. | : 11/428996 | |
| DATED | : February 2, 2010 | |
| INVENTOR(S) | : Bruce Kirke Bieneman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 653 days.

Signed and Sealed this

Twenty-third Day of November, 2010

David J. Kappos
*Director of the United States Patent and Trademark Office*